US 6,638,304 B2

(12) United States Patent
Azar

(10) Patent No.: US 6,638,304 B2
(45) Date of Patent: Oct. 28, 2003

(54) VISION PROSTHESIS

(75) Inventor: Dimitri Azar, Brookline, MA (US)

(73) Assignee: Massachusetts Eye & Ear Infirmary, Boston, MA (US)

( * ) Notice: Subject to any disclaimer, the term of this patent is extended or adjusted under 35 U.S.C. 154(b) by 0 days.

(21) Appl. No.: 09/909,933

(22) Filed: Jul. 20, 2001

(65) Prior Publication Data

US 2003/0018383 A1 Jan. 23, 2003

(51) Int. Cl.⁷ .................................................. A61F 2/16
(52) U.S. Cl. ...................... 623/6.22; 623/6.34; 623/6.37
(58) Field of Search ............................... 623/4.1, 5.11, 623/6.11, 6.22, 6.32, 6.34, 6.37; 396/75, 76, 77, 89; 351/41, 57, 158, 168

(56) References Cited

U.S. PATENT DOCUMENTS

| | | | |
|---|---|---|---|
| 4,190,330 A | 2/1980 | Berreman | 350/331 |
| 4,230,942 A | 10/1980 | Stauffer | 250/204 |
| 4,309,603 A | 1/1982 | Stauffer | 250/204 |
| 4,466,703 A | 8/1984 | Nishimoto | 350/379 |
| 4,601,545 A * | 7/1986 | Kern | 349/139 |
| 4,787,903 A * | 11/1988 | Grendahl | 623/6.22 |
| 5,182,585 A | 1/1993 | Stoner | 351/41 |
| 5,359,444 A * | 10/1994 | Piosenka et al. | 349/13 |
| 5,593,437 A * | 1/1997 | Arita et al. | 351/158 |
| 5,800,530 A | 9/1998 | Rizzo, III | 623/6 |

* cited by examiner

Primary Examiner—Corrine McDermott
Assistant Examiner—William H. Matthews
(74) Attorney, Agent, or Firm—Fish & Richardson P.C.

(57) ABSTRACT

A vision prosthesis includes a lens having an index of refraction that varies in response to a focusing stimulus. An actuator in communication with the lens provides the focusing stimulus on the basis of a range estimate from a rangefinder. A controller coupled to the rangefinder and to the actuator causes the actuator to generate a focusing stimulus on the basis of the range estimate.

96 Claims, 10 Drawing Sheets

VISION PROSTHESIS

FIELD OF INVENTION

This invention relates to a vision prosthesis, and in particular, to prosthetic lenses.

BACKGROUND

In the course of daily life, one typically regards objects located at different distances from the eye. To selectively focus on such objects, the focal length of the eye's lens must change. In a healthy eye, this is achieved through the contraction of a ciliary muscle that is mechanically coupled to the lens. To the extent that the ciliary muscle contracts, it deforms the lens. This deformation changes the focal length of the lens. By selectively deforming the lens in this manner, it becomes possible to focus on objects that are at different distances from the eye. This process of selectively focusing on objects at different distances is referred to as "accommodation".

As a person ages, the lens loses plasticity. As a result, it becomes increasingly difficult to deform the lens sufficiently to focus on objects at different distances. To compensate for this loss of function, it is necessary to provide different optical corrections for focusing on objects at different distances.

One approach to applying different optical corrections is to carry different pairs of glasses and to swap glasses as the need arises. For example, one might carry reading glasses for reading and a separate pair of distance glasses for driving. This is inconvenient both because of the need to carry more than one pair of glasses and because of the need to swap glasses frequently.

Bifocal lenses assist accommodation by integrating two different optical corrections onto the same lens. The lower part of the lens is ground to provide a correction suitable for reading or other close-up work while the remainder of the lens is ground to provide a correction for distance vision. To regard an object, a wearer of a bifocal lens need only maneuver the head so that rays extending between the object-of-regard and the pupil pass through that portion of the bifocal lens having an optical correction appropriate for the range to that object.

The concept of a bifocal lens, in which different optical corrections are integrated into the same lens, has been generalized to include trifocal lenses, in which three different optical corrections are integrated into the same lens, and continuous gradient lenses in which a continuum of optical corrections are integrated into the same lens. However, just as in the case of bifocal lenses, optical correction for different ranges of distance using these multifocal lenses relies extensively on relative motion between the pupil and the lens.

Once a lens is implanted in the eye, the lens and the pupil move together as a unit. Thus, no matter how the patient's head is tilted, rays extending between the object-of-regard and the pupil cannot be made to pass through a selected portion of the implanted lens. As a result, multifocal lenses are generally unsuitable for intraocular implantation because once the lens is implanted into the eye, there can be no longer be relative motion between the lens and the pupil.

A lens suitable for intraocular implantation is therefore generally restricted to being a single focus lens. Such a lens can provide optical correction for only a single range of distances. A patient who has had such a lens implanted into the eye must therefore continue to wear glasses to provide optical corrections for those distances that are not accommodated by the intraocular lens.

SUMMARY

The invention provides a vision prosthesis for restoring a patient's ability to focus on objects at different distances. The vision prosthesis includes a lens whose focal length can automatically be changed, and a rangefinder coupled to that lens for estimating the range to an object that the patient wishes to focus on.

In one embodiment, the variable-focus lens of the vision prosthesis has an index of refraction that varies in response to a focusing stimulus. An actuator in communication with the lens provides the necessary focusing stimulus on the basis of a range estimate from the rangefinder. A controller coupled to the rangefinder and to the actuator causes the actuator to generate a focusing stimulus on the basis of this range estimate.

Because it is the index of refraction that is changed, the vision prosthesis provides control over the focal length of the lens without the need to mechanically move the lens or any portions thereof. The vision prosthesis thus provides a lens of variable focal length with no moving parts and without the complexity and excessive power consumption associated with a moveable system.

The lens of the vision prosthesis can be adapted for implantation in an eye of a phakic or an aphakic human patient. Alternatively, the lens, and its associated electronics, can be worn outside the patient on, for example, an eyeglass frame.

When implanted in the eye, the lens can be disposed at a variety of locations, such as the anterior chamber, the posterior chamber, the lens bag, or the cornea. To ease the implantation process and to minimize the extent of the incision required, the lens can be a foldable lens having a tendency to spring back into an unfolded state.

In one embodiment of the vision prosthesis, the lens includes a chamber containing a nematic liquid crystal or other material that has a changeable index of refraction. A nematic liquid crystal has an index of refraction that changes in response to an applied electromagnetic field. This change in the index of refraction results in a change in the focal length of the lens.

The actuator for the lens can include a variable voltage source and one or more electrodes coupled to both the variable voltage source and the lens. Alternatively, the actuator can include a variable current source and one or more coils coupled to the variable current source and to the lens. In either case, the actuator generates a field, an electric field in the former case and a magnetic field in the latter case, that can interact with the nematic liquid crystal to selectively alter its index of refraction.

The index of refraction of the lens need not be spatially uniform. By providing a plurality of actuating elements coupled to different local regions of the lens, the index of refraction can be varied at those local regions. This enables the lens to have an effective optical shape that is largely independent of its physical shape. A convex lens can be created, for example, by applying a stronger electric field to the central portion of a planar chamber filled with nematic liquid crystal than to the periphery. This changes the index of refraction at the center more than at the periphery. A lens having a spatially non-uniform index of refraction can be implemented by providing a plurality of electrodes disposed at different portions of the lens. In one aspect of the invention, these electrodes are concentric electrodes. In such a case, the index of refraction can be made a function of distance from the center of the lens.

In an alternative embodiment, the index of refraction can be made a function of more than one spatial variable. For example, the electrodes can be distributed in a two-dimensional grid on the surface of the lens. Such a grid can be a polar grid or a rectilinear grid. Its primary function would be to correct wavefront aberrations present in the eye due to abnormalities in the cornea, the lens, and the ocular media.

An advantage of a lens having planar chamber as described above is that such a lens can be made thin enough to be implanted in very small spaces within the eye. For example, a lens in which first and second planar sides are separated by a gap smaller than the separation between the lens bag in an eye and the iris in the eye can be implanted in the posterior chamber of the eye.

In some cases, it may not be possible to vary the index of refraction sufficiently to correct the patient's vision. In such cases, the lens can include one or more lens elements that can be moved so as to bring an image into focus. Such a lens also includes a motor to move the lens elements.

Alternatively, the lens can have a baseline curvature and also be filled with nematic crystal or a material having an index of refraction that can be changed. The baseline curvature can be used to perform a gross correction that can be fine-tuned by locally varying the index of refraction of the lens material.

In one embodiment of the vision prosthesis, the rangefinder includes a transducer for detecting a stimulus from an anatomic structure in an eye, the stimulus being indicative of a range to the object-of-regard. The transducer can be a pressure transducer for detecting contraction of a muscle, such as a piezoelectric element that generates a voltage in response to contraction of the muscle. Alternatively, the transducer can be an electromyograph for detecting electrical activity associated with contraction of the muscle.

The stimulus detected by the transducer can come from the activities or states of one or more anatomical structures within the eye. These activities or states include: contraction of a ciliary muscle, tension in a zonule, mechanical disturbance of a lens bag, contraction of a rectus muscle, and dilation of an iris.

The rangefinder of the vision prosthesis does not, however, have to rely on the operation of any structure in eye to estimate a distance to an object. For example, the rangefinder can also include an autofocus system. One example of an autofocus system includes: an infrared transmitter for illuminating an object with an infrared beam; an infrared receiver for receiving a reflected beam from the object, and a processor coupled to the infrared receiver for estimating a range to the object on the basis of the reflected beam. However, other autofocusing systems can readily be adapted for the use in the vision prosthesis.

To assist the autofocus system in achieving and maintaining focus, it is often desirable to include a feedback loop coupled to the autofocus system. One example of a feedback loop includes first and second lenslets posterior to the lens. Each lenslet is in optical communication with an associated photodetector posterior to that lenslet. The distance between the lenslet and its associated photodetector is between the focal lengths of the two lenslets.

Regardless of the type of rangefinder, it is useful to provide an optional manual focusing control for enabling a patient to fine tune focusing of the lens. A manual focusing control enables the patient to correct compensate for minor inaccuracies in the signal provided by the automatic focusing system. With a manual focusing control, the rangefinder can in fact be dispensed with. Thus, in yet another embodiment of the invention, the apparatus includes a manual focusing control instead of a rangefinder.

These and other features and advantages of the invention will be apparent from the following detailed description and the accompanying figures, in which:

DETAILED DESCRIPTION

Figure 1:
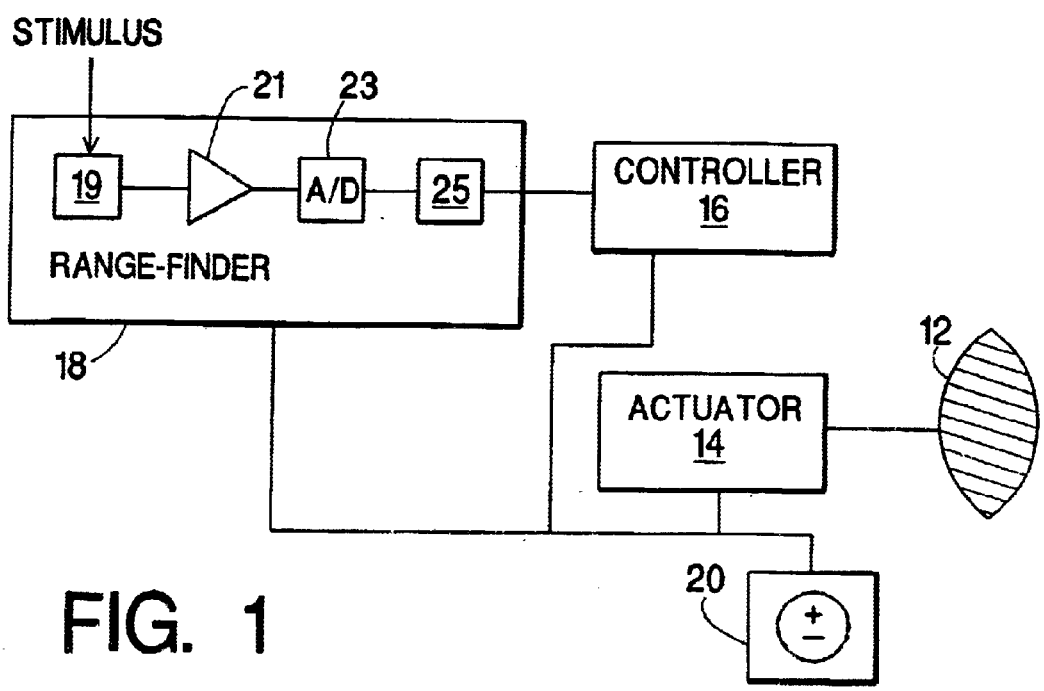
FIG. 1 is a block diagram of the vision prosthesis.

FIG. 1 shows a block diagram of a vision prosthesis 10 having a lens 12 whose index of refraction can be made to vary in response to a focusing signal provided to the lens 12 by an actuator 14. The lens 12 directs light through a nematic liquid-crystal whose index of refraction varies in response to an applied electric field. The actuator 14 includes one or more electrodes in electrical communication with the lens 12. However, the lens 12 can also direct light through a material whose index of refraction varies in response to an applied magnetic field. In this case, the actuator 14 is a magnetic field source, such as a current-carrying coil, in magnetic communication with the lens 12.

Throughout this specification, the terms "lens" and "intraocular lens" refer to the prosthetic lens that is part of the vision prosthesis 10. The lens that is an anatomical structure within the eye is referred to as the "natural lens".

The nature of the focusing signal provided by the actuator 14 controls the extent to which the index of refraction is changed. The actuator 14 generates a focusing signal in response to instructions from a controller 16 in communication with the actuator 14.

The controller 16 is typically a microcontroller having instructions encoded therein. These instructions can be implemented as software or firmware. However, the instructions can also be encoded directly in hardware in, for example, an application-specific integrated circuit. The instructions provided to the microcontroller include instructions for receiving, from a rangefinder 18, data indicative of the distance to an object-of-regard, and instructions for processing that data to obtain a focusing signal. The focusing signal alters the lens' index of refraction to focus an image of the object-of-regard on the retina.

The rangefinder 18 typically includes a transducer 19 for detecting a stimulus from which a range to an object can be inferred. The signal generated by the transducer 19 often requires amplification before it is of sufficient power to provide to the controller 16. Additionally, the signal may require some preliminary signal conditioning. Accordingly, in addition to a transducer 19, the rangefinder 18 includes an amplifier 21 to amplify the signal, an A/D converter 23 to sample the resultant amplified signal, and a digital signal processor 25 to receive the sampled signal. The output of the digital signal processor 25 is provided to the controller 16.

A power source 20 supplies power to the controller 16, the range finder 18, and the actuator 14. A single power source 20 can provide power to all three components. However, the vision prosthesis 10 can also include a separate power source 20 for any combination of those components that require power.

1. Intraocular Vision Prosthesis 1.1 Lens and Actuator

Figure 2:
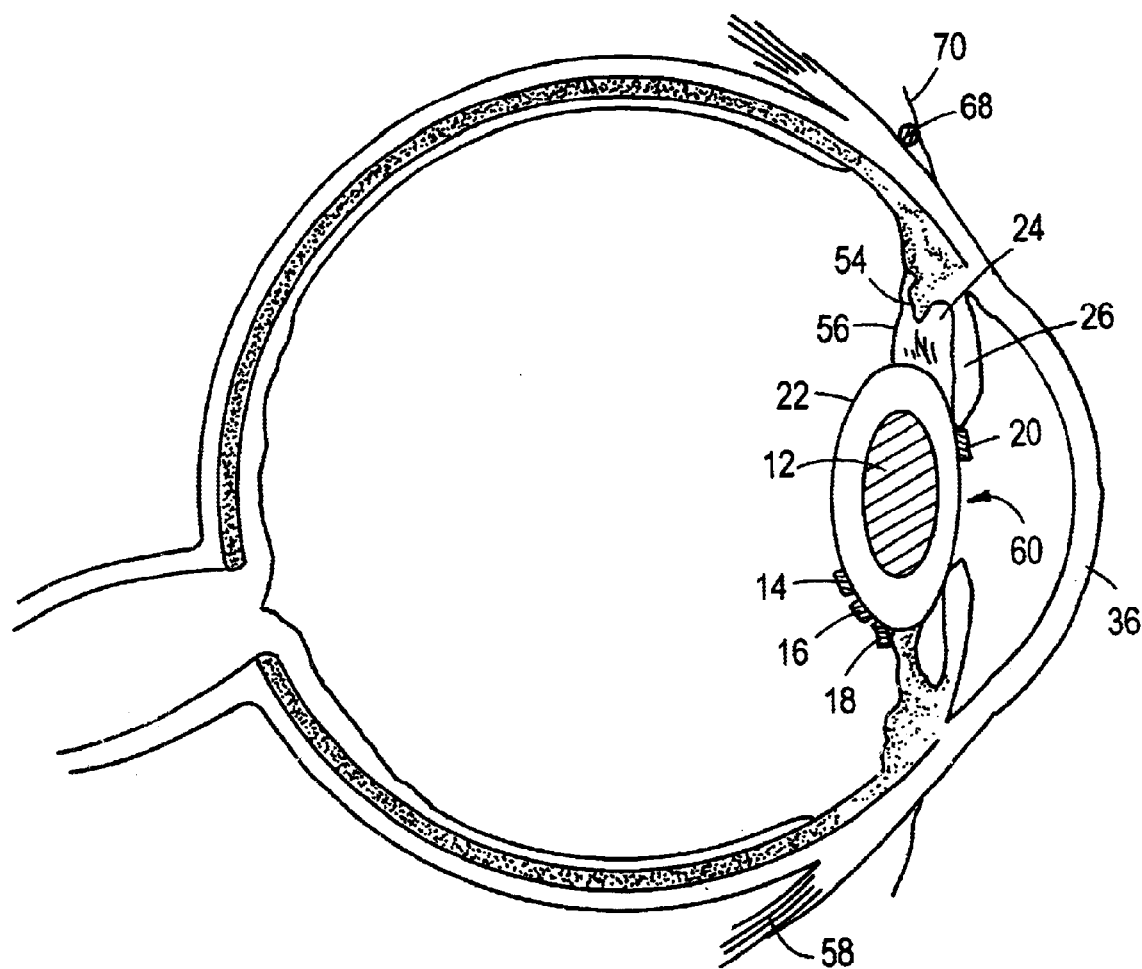
FIGS. 2–5 show the vision prosthesis of FIG. 1 implanted at various locations within the eye.
Figure 3:
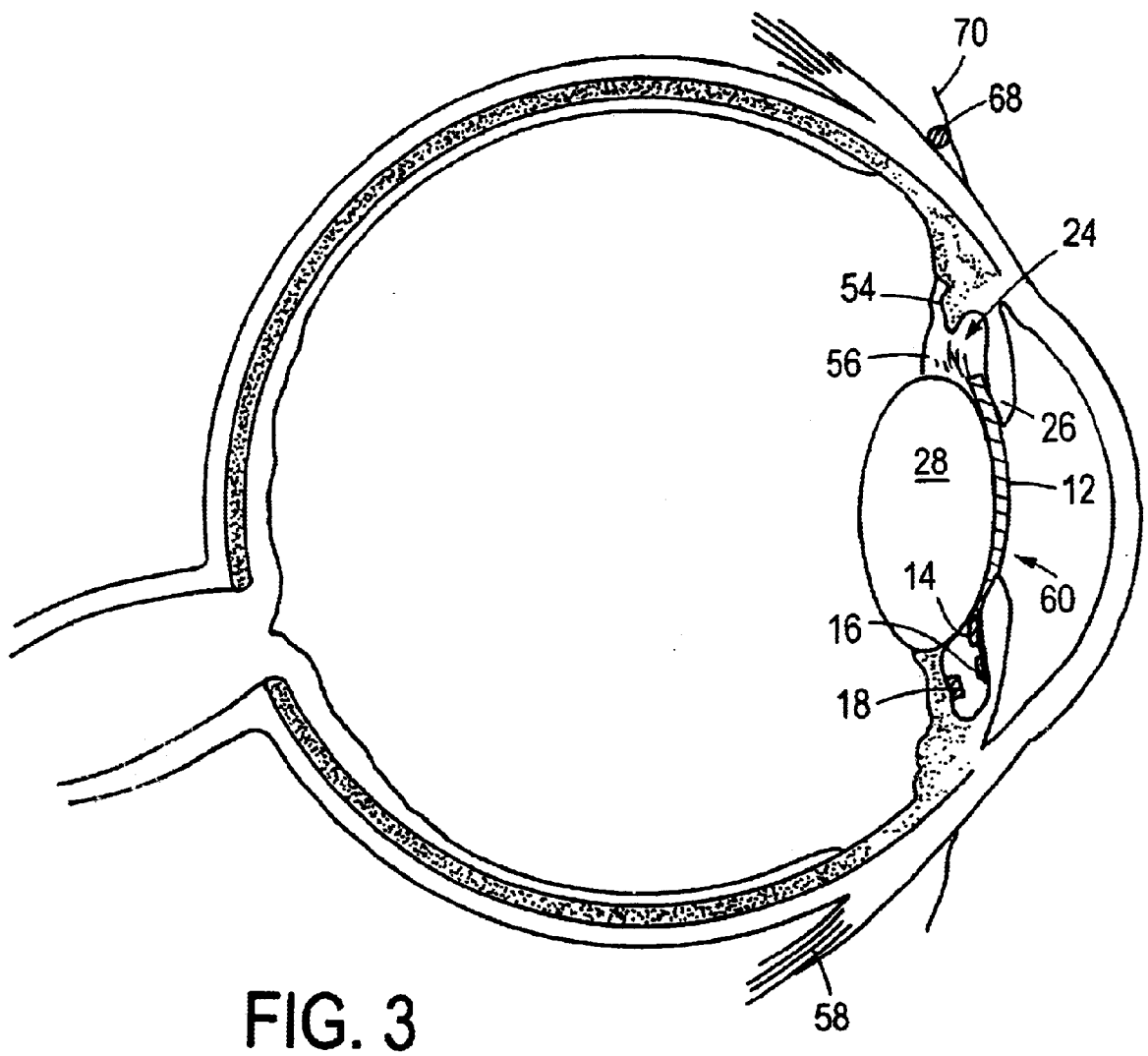
Figure 4:
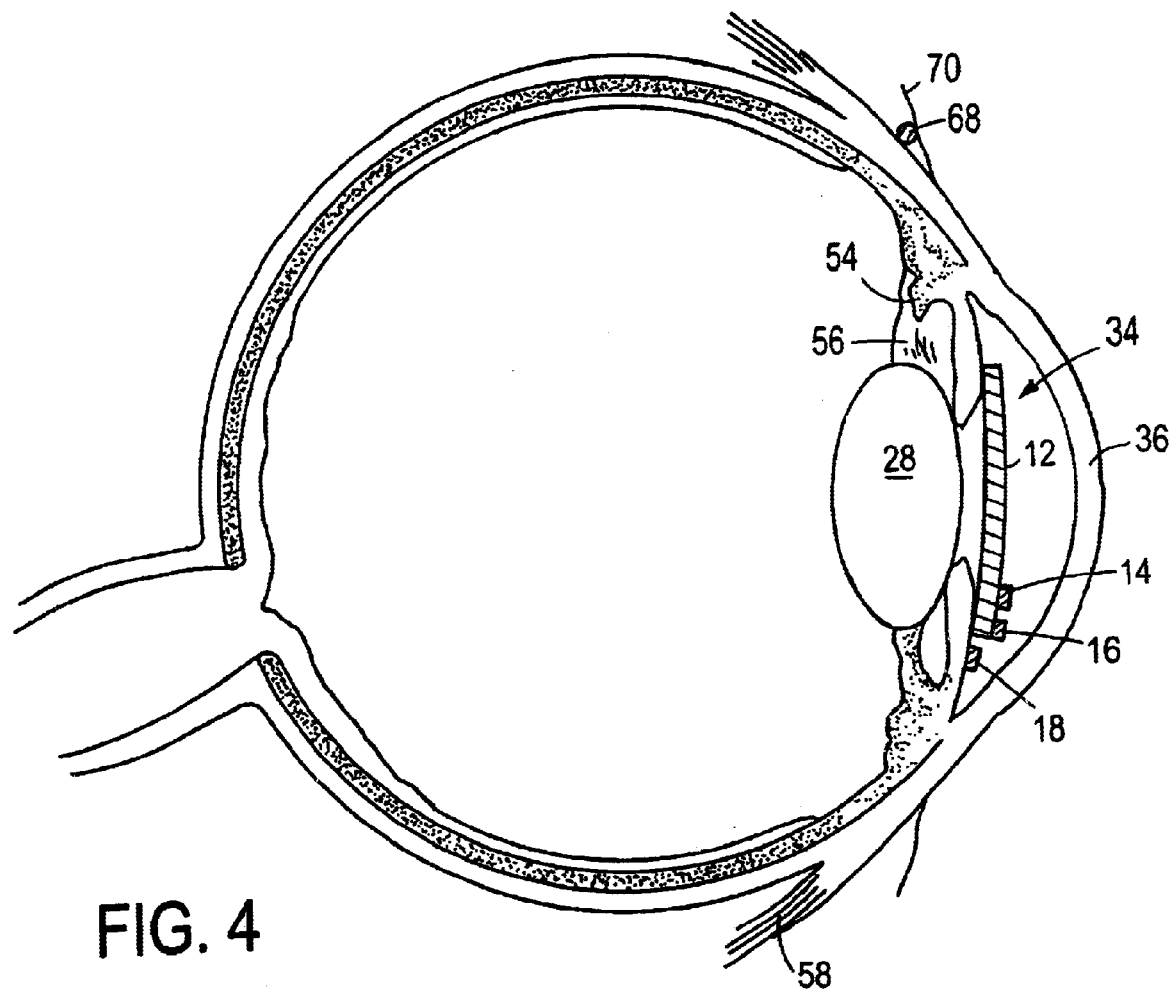
Figure 5:
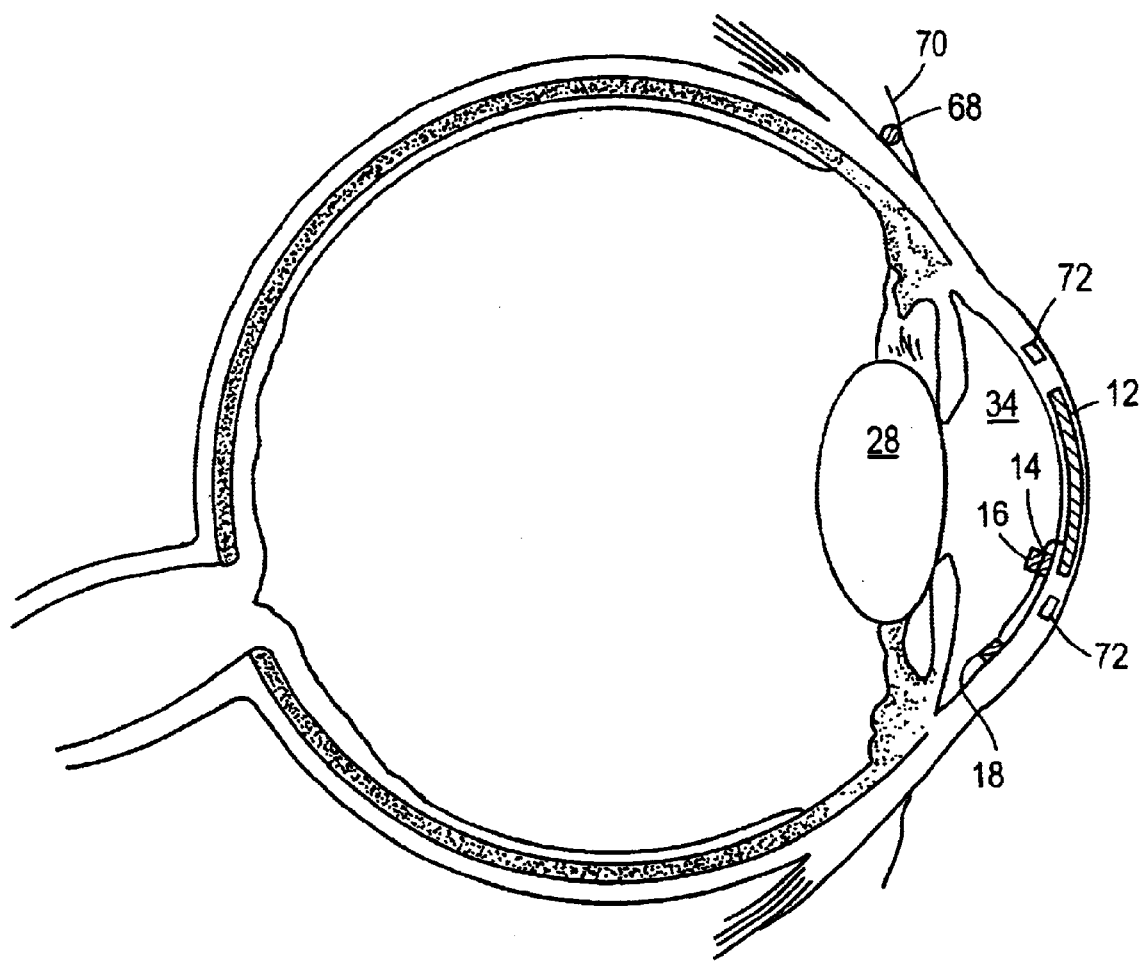

In one embodiment of the vision prosthesis 10, the lens 12 is an intraocular lens. The intraocular lens 12 can be implanted into an aphakic patient, as shown in FIG. 2, in which case it can be implanted into the lens-bag 22 from which the patient's natural lens has been removed. Alternatively, the intraocular lens 12 can be implanted into a phakic patient, in which case it can be implanted into the posterior chamber 24, between the iris 26 and the patient's natural lens 28, as shown in FIG. 3. With the intraocular lens 12 implanted in the posterior chamber 24, the haptic 30 of the lens 12 rests in the sulcus 32. The intraocular lens 12 can also be implanted in the anterior chamber 34, as shown in FIG. 4, or in the cornea 36, as shown in FIG. 5.

Preferably, the lens 12 is a foldable lens having a tendency to spring back to its unfolded position. Such a lens 12 can be inserted through a small incision, maneuvered into the desired location, and released. Once released, the lens 12 springs back to its unfolded position.

Figure 6:
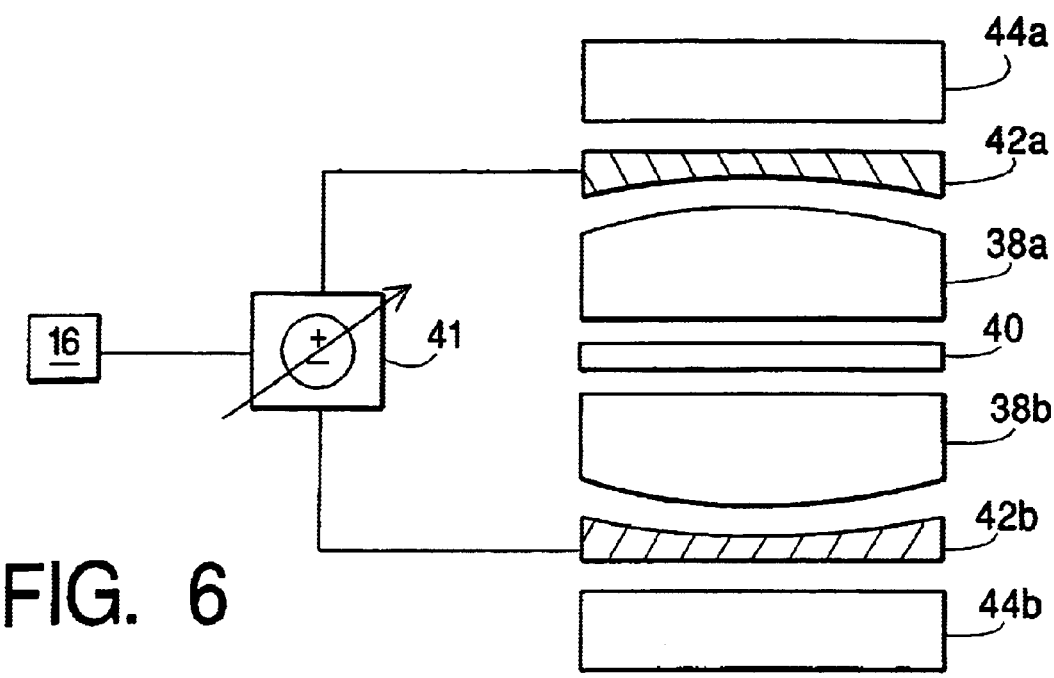
FIGS. 6, 7A, and 7B show two embodiments of the lens and actuator of FIG. 1.

In one embodiment of the lens 12, shown in exploded view in FIG. 6, first and second curved chambers 38a, 38b filled with nematic liquid-crystal are separated by a transparent plate 40. In this embodiment, the actuator 14 includes a variable voltage source 41 connected to two transparent electrodes 42a, 42b disposed on an outer surface of each curved chamber 38a, 38b. The variable voltage source 41 generates a variable voltage in response to instructions from the controller 16. First and second transparent outer layers 44a, 44b cover the first and second electrodes 42a, 42b respectively.

When the variable voltage source 41 applies a voltage, the first and second electrodes 42a, 42b impose an electric field in the nematic liquid-crystal. This electric field tends to reorient the directors of the nematic liquid-crystal, thereby changing its index of refraction. A lens assembly of this type is described fully in U.S. Pat. No. 4,190,330, the contents of which are herein incorporated by reference.

Figure 7A:
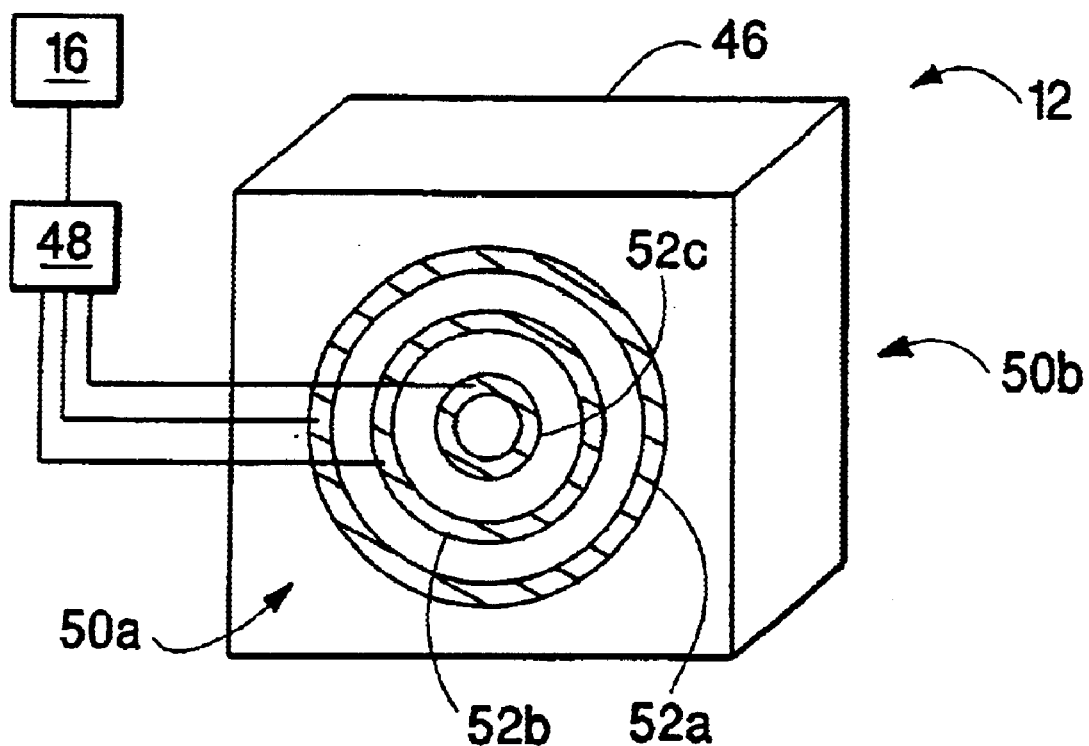

In another embodiment, shown in FIG. 7A, the lens 12 includes a thin chamber 46 filled with nematic liquid-crystal and the actuator 14 includes a variable voltage source 48 and first and second sets 50a, 50b of electrodes 52a–c disposed on opposed planar surfaces of the thin chamber 46. Each of the electrodes 52a–c is individually addressable by the controller 16. A voltage maintained across a electrode 52a form the first set 50a and a corresponding electrode from the second set 50b results in an electric field across a local zone of the nematic liquid-crystal adjacent to those electrodes. This electric field reorients the directors, and hence alters the index of refraction, within that zone. As a result, the index of refraction can be made to vary at different points of the lens 12.

Figure 7B:
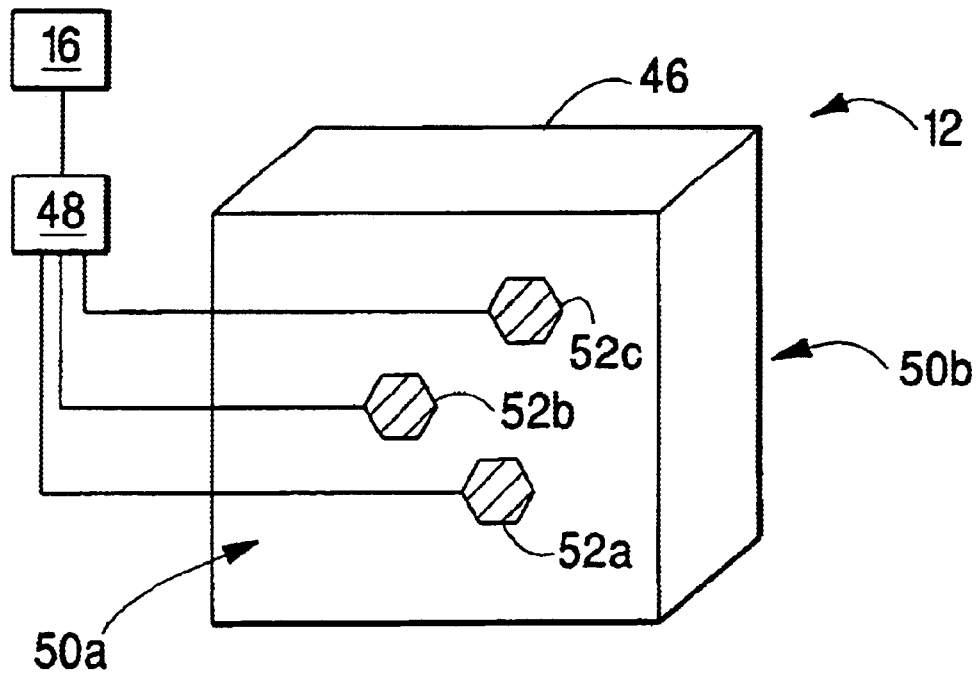

FIG. 7A shows a lens assembly having concentric electrodes 52a–c. A lens assembly of this type is described fully in U.S. Pat. No. 4,466,703, the contents of which are herein incorporated by reference. In this embodiment, the index of refraction can be altered as a function of distance from the center of the lens 12. However, individually addressable electrodes 52a–c can also be arranged in a two-dimensional array on the surface of the lens 12. When this is the case, the index of refraction can be varied as a function of two spatial variables. The grid of electrodes 52a–c can be a polar grid, as shown in FIG. 7A, or a rectilinear grid, as shown in FIG. 7B. The electrodes 52a–c can be distributed uniformly on the grid, or they can be distributed more sparsely in certain regions of the lens 12 and more densely in other regions of the lens 12.

Because of its thin planar structure, a lens 12 of the type shown in FIG. 6 is particularly suitable for implantation in constricted spaces, such as in the posterior chamber 24 of a phakic patient, as shown in FIG. 3.

In another embodiment, the lens 12 includes a chamber filled with a nematic liquid-crystal and the actuator 14 is a current-carrying coil that generates a magnetic field. In this embodiment, the controller 16 causes current to flow in the coil. This current supports a magnetic field that reorients the directors in the nematic liquid-crystal. This results in a change in the liquid crystal's index of refraction.

The extent to which the index of refraction of a nematic liquid crystal can be changed is limited. Once all the directors in the nematic liquid crystal have been polarized, increasing the magnitude of the imposed electric field has no further effect. A nematic liquid crystal in this state is said to be saturated. To change the focal length beyond the point at which the nematic crystal is saturated, a lens 12 can also include one or more lens elements that are moved relative to each other by micromechanical motors.

Alternatively, the lens can have a baseline curvature that and also be filled with nematic crystal. The baseline curvature can be used to perform a gross correction that can be fine-tuned by locally varying the index of refraction of the lens material.

In another embodiment, the lens is made up of a multiplicity of lenslets, as shown in FIG. 7B, each of which has its own baseline curvature and each of which is filled with nematic crystal. An individually addressable electrode is then connected to each of the lenslets. In this embodiment, both the lens curvature and the index of refraction can be varied locally and can be varied as a function of two spatial variables.

1.2 Rangefinder

In a normal eye, contraction of a ciliary muscle 54 is transmitted to the natural lens 28 by zonules 56 extending between the ciliary muscle 54 and the lens-bag 22. When the object-of-regard is nearby, the ciliary muscle 54 contracts, thereby deforming the natural lens 28 so as to bring an image of the object into focus on the retina. When the object-of-regard is distant, the ciliary muscle 54 relaxes, thereby restoring the natural lens 28 to a shape that brings distant objects into focus on the retina. The activity of the ciliary muscle 54 thus provides an indication of the range to an object-of-regard.

For an intraocular lens 12, the transducer 19 of the rangefinder 18 can be a transducer for detecting contraction of the ciliary muscle 54. In one embodiment, the rangefinder 18 can include a pressure transducer that detects the mechanical activity of the ciliary muscle 54. A pressure transducer coupled to the ciliary muscle 54 can be a piezoelectric device that deforms, and hence generates a voltage, in response to contraction of the ciliary muscle 54. In another embodiment, the transducer can include an electromyograph for detecting electrical activity within the ciliary muscle 54.

As noted above, the activity of the ciliary muscle 54 is transmitted to the natural lens 28 by zonules 56 extending between the ciliary muscle 54 and the lens-bag 22. Both the tension in the zonules 56 and the resulting mechanical disturbance of the lens-bag 22 can be also be used as indicators of the distance to the object-of-regard. In recognition of this, the rangefinder 18 can also include a tension measuring transducer in communication with the zonules 56 or a motion sensing transducer in communication with the lens-bag 22. These sensors can likewise be piezoelectric devices that generate a voltage in response to mechanical stimuli.

The activity of the rectus muscles 58 can also be used to infer the distance to an object-of-regard. For example, a contraction of the rectus muscles 58 that would cause the eye to converge medially can suggest that the object-of-regard is nearby, whereas contraction of the rectus muscles 58 that would cause the eye to gaze forward might suggest that the object-of-regard is distant. The rangefinder 18 can thus include a transducer that responds to either mechanical motion of the rectus muscles 58 or to the electrical activity that triggers that mechanical motion.

It is also known that when a person intends to focus on a nearby object, the iris 26 contracts the pupil 60. Another embodiment of the rangefinder 18 relies on this contraction to provide information indicative of the distance to the object-of-regard. In this embodiment, the rangefinder 18 includes a transducer, similar to that described above in connection with the rangefinder 18 that uses ciliary muscle or rectus muscle activity, to estimate the distance to the object-of-regard. Additionally, since contraction of the pupil 60 diminishes the light incident on the lens 12, the transducer 19 of the rangefinder 18 can include a photodetector for detecting this change in the light.

The foregoing embodiments of the rangefinder 18 are intended to be implanted into a patient, where they can be coupled to the anatomical structures of the eye. This configuration, in which the dynamic properties of one or more anatomical structures of the eye are used to infer the distance to an object-of-regard, is advantageous because those properties are under the patient's control. As a result, the patient can, to a certain extent, provide feedback to the rangefinder 18 by controlling those dynamic properties. For example, where the rangefinder 18 includes a transducer responsive to the ciliary muscle 54, the patient can control the index of refraction of the intraocular lens 12 by appropriately contracting or relaxing the ciliary muscle 54.

Other embodiments of the rangefinder 18 can provide an estimate of the range without relying on stimuli from anatomic structures of the eye. For example, a rangefinder 18 similar to that used in an auto-focus camera can be implanted. An example of such a rangefinder 18 is one that transmits a beam of infrared radiation, detects a reflected beam, and estimates range on the basis of that reflected beam. The output of the rangefinder 18 can then be communicated to the actuator 14. Since a rangefinder 18 of this type does not rely on stimuli from anatomic structures of the eye, it need not be implanted in the eye at all. Instead, it can be worn on an eyeglass frame or even hand-held and pointed at objects of regard. In such a case, the signal from the rangefinder 18 can be communicated to the actuator 14 either by a wire connected to an implanted actuator 14 or by a wireless link.

A rangefinder 18 that does not rely on stimuli from an anatomic structure within the eye no longer enjoys feedback from the patient. As a result, it is desirable to provide a feedback mechanism to enhance the range-finder's ability to achieve and maintain focus on an object-of-regard.

Figure 8:
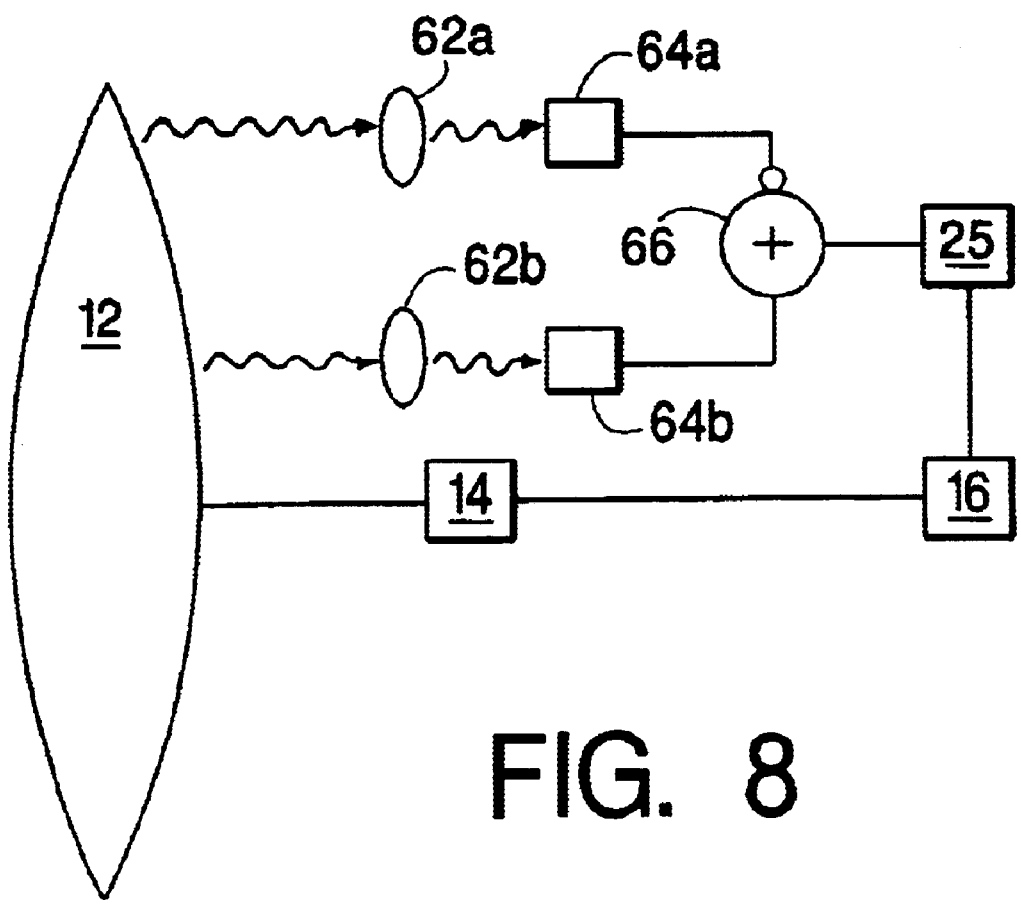
FIG. 8 shows a feedback mechanism for a rangefinder of the vision prosthesis of FIG. 1.

In a feedback mechanism as shown in FIG. 8, first and second lenslets 62a, 62b are disposed posterior to the intraocular lens 12. The first and second lenslets 62a, 62b are preferably disposed near the periphery of the intraocular lens 12 to avoid interfering with the patient's vision. A first photodetector 64a is disposed at a selected distance posterior to the first lenslet 62a, and a second photodetector 64b is disposed at the same selected distance posterior to the second lenslet 62b. The focal length of the first lenslet 62a is slightly greater than the selected distance, whereas the focal length of the second lenslet 62b is slightly less than the selected distance.

The outputs of the first and second photodetectors 64a, 64b are connected to a differencing element 66 that evaluates the difference between their output. This is difference is provided to the digital signal processor 25. When the output of the differencing element 66 is zero, the intraocular lens 12 is in focus. When the output of the differencing element 66 is non-zero, the sign of the output identifies whether the focal length of the intraocular lens 12 needs to be increased or decreased, and the magnitude of the output determines the extent to which the focal length of the intraocular lens 12 needs to change to bring the lens 12 into focus. A feedback mechanism of this type is disclosed in U.S. Pat. No. 4,309,603, the contents of which are herein incorporated by reference.

In any of the above embodiments of the rangefinder 18, a manual control can also be provided to enable a patient to fine-tune the focusing signal. The digital signal processor 25 can then use any correction provided by the user to calibrate the range estimates provided by the rangefinder 18 so that the next time that that range estimate is received, the focusing signal provided by the digital signal processor 25 will no longer need fine-tuning by the patient. This results in a self-calibrating vision prosthesis 10.

The choice of which of the above range-finders is to be used depends on the particular application. For example, a lens 12 implanted in the posterior chamber 24 has ready access to the ciliary muscle 54 near the haptic 30 of the lens 12. Under these circumstances, a rangefinder that detects ciliary muscle activity is a suitable choice. A lens 12 implanted in the anterior chamber 34 is conveniently located relative to the iris 26 but cannot easily be coupled to the ciliary muscle 54. Hence, under these circumstances, a rangefinder that detects contraction of the iris 26 is a suitable choice. A lens 12 implanted in the cornea 36 is conveniently located relative to the rectus muscles 58. Hence, under these circumstances, a rangefinder that detects contraction of the rectus muscles 58 is a suitable choice. In the case of an aphakic patient, in which the natural lens 28 in the lens-bag 22 has been replaced by an intraocular lens 12, a rangefinder that detects zonule tension or mechanical disturbances of the lens-bag 22 is a suitable choice. In patients having a loss of function in any of the foregoing anatomical structures, a rangefinder that incorporates an automatic focusing system similar to that used in an autofocus camera is a suitable choice.

1.3 Power Source

As noted above, the controller 16, the rangefinder 18, and the actuator 14 shown in FIG. 1 require a power source 20. In one embodiment, the power source 20 can be an implanted battery 68. The battery 68 can be implanted in any convenient location, such as under the conjunctiva 70 in the Therron's capsule, or within the sclera. Unless it is rechargeable in situ, such a power source 20 will periodically require replacement.

In another embodiment, the power source 20 can be a photovoltaic cell 72 implanted in a portion of the eye that receives sufficient light to power the vision prosthesis 10. The photovoltaic cell 72 can be mounted on a peripheral portion of the lens 12 where it will receive adequate light without interfering excessively with vision. Alternatively, the photovoltaic cell 72 can be implanted within the cornea 36, where it will receive considerably more light. When implanted into the cornea 36, the photovoltaic cell 72 can take the form of an annulus or a portion of an annulus centered at the center of the cornea 36. This configuration avoids excessive interference with the patient's vision while providing sufficient area for collection of light.

Power generated by such a photovoltaic cell 72 can also be used to recharge a battery 68, thereby enabling the vision prosthesis 10 to operate under low-light conditions. The use of a photovoltaic cell as a power source 20 eliminates the need for the patient to undergo the invasive procedure of replacing an implanted battery 68.

The choice of a power source 20 depends in part on the relative locations of the components that are to be supplied with power and the ease with which connections can be made to those components. When the lens 12 is implanted in the cornea 36, for example, the associated electronics are likely to be accessible to a photovoltaic cell 72 also implanted in the cornea 36. In addition, a rechargeable subconjunctival battery 68 is also easily accessible to the photovoltaic cell 72. The disposition of one or more photovoltaic cells 72 in an annular region at the periphery of the cornea 36 maximizes the exposure of the photovoltaic cells 72 to ambient light.

When the lens 12 is implanted in the anterior chamber 34, one or more photovoltaic cells 72 are arranged in an annular region on the periphery of the lens 12. This reduces interference with the patient's vision while providing sufficient area for exposure to ambient light. For a lens 12 implanted in the anterior chamber 34, a rechargeable battery 68 implanted beneath the conjunctiva 70 continues to be conveniently located relative to the photovoltaic cells 72.

When the lens 12 is implanted in the posterior chamber 24, one or more photovoltaic cells 72 can be arranged in an annular region of the lens 12. However, in this case, the periphery of the lens 12 is often shaded by the iris 26 as it contracts to narrow the pupil 60. Because of this, photovoltaic cells 72 disposed around the periphery of the lens 12 may receive insufficient light to power the various other components of the vision prosthesis 10. As a result, it becomes preferable to dispose the photovoltaic cells 72 in an annular region having radius small enough to ensure adequate lighting but large enough to avoid excessive interference with the patient's vision.

2. Extraocular Vision Prosthesis

The lens 12 in FIG. 1 need not be an intraocular lens. In an alternative embodiment, shown in FIG. 9, the vision prosthesis 10, including the lens 12, is mounted on a frame 74 and worn in the manner of conventional eyeglasses. This embodiment largely eliminates those constraints on the size and location of the power source 20 that are imposed by the relative inaccessibility of the various anatomical structures of the eye as well as by the limited volume surrounding them.

Figure 9:
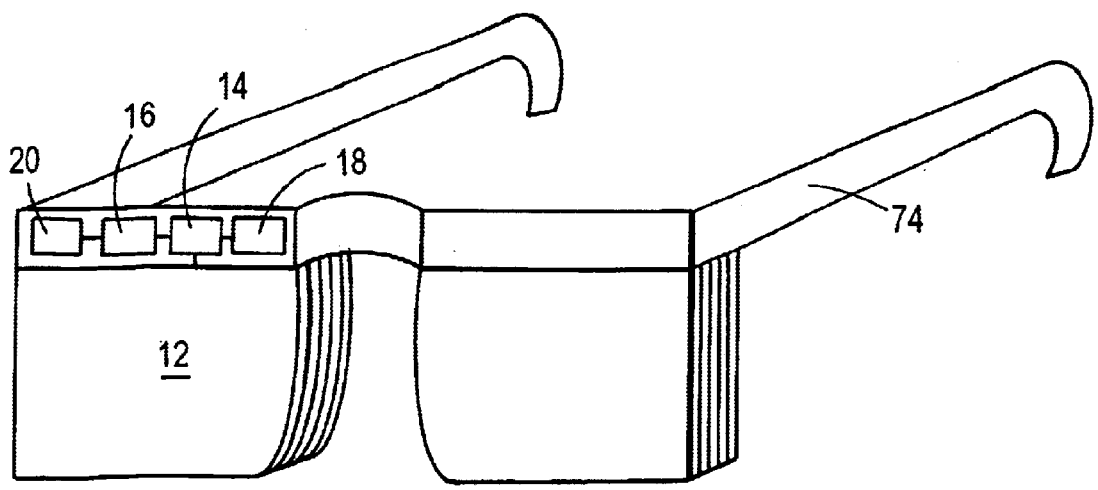
FIG. 9 shows the vision prosthesis of FIG. 1 mounted on an eyeglass frame.

In the embodiment shown in FIG. 9, the rangefinder 18 is typically of the type used in an autofocus camera together with the two-lenslet feedback mechanism described above in connection with the intraocular vision prosthesis 10. The lens 12, its associated actuator 14, and the power source 20 can be selected from any of the types already described above in connection with the intraocular embodiment of the vision prosthesis 10.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Having described the invention, and a preferred embodiment thereof, what I claim as new and secured by letters patent is:

1. An apparatus comprising:
    a lens having an index of refraction that varies in response to a focusing stimulus; the lens including a first lens element;
    a second lens element moveable relative to said first lens element; and
    a motor coupled to said second lens element for moving said second lens element relative to said first lens element,
    an actuator in communication with said lens for providing said focusing stimulus;
    a rangefinder for generating, from a range estimate, a relative distance to an object-of-regard; and
    a controller coupled to said rangefinder and to said actuator for causing said actuator to generate a focusing stimulus on the basis of said range estimate.

2. The apparatus of claim 1, wherein said lens is adapted for implantation in an eye of a human patient.

3. The apparatus of claim 2, wherein said lens is adapted for implantation at a location in an eye, said location being selected from the group consisting of:
    the anterior chamber;
    the posterior chamber;
    the lens bag; and
    the cornea.

4. The apparatus of claim 2, wherein said lens is adapted for implantation in an aphakic human patient.

5. The apparatus of claim 2, wherein said lens is adapted for implantation in a phakic human patient.

6. The apparatus of claim 1, wherein said lens is a foldable lens having a tendency to spring back into an unfolded state.

7. The apparatus of claim 1, wherein said lens comprises a chamber containing nematic liquid crystal.

8. The apparatus of claim 7, wherein said chamber comprises a first planar side and a second planar side opposed to said first planar side, said first and second planar sides being separated by a gap smaller than a separation between a lens bag in an eye and an iris in said eye.

9. The apparatus of claim 1, wherein said actuator comprises a variable voltage source.

10. The apparatus of claim 9, wherein said actuator further comprises an electrode coupled to said variable voltage source and to said lens for applying an electric field within said lens.

11. The apparatus of claim 1, wherein said actuator comprises a plurality of actuating elements coupled to different local regions of said lens for selectively varying said index of refraction at said different local regions of said lens.

12. The apparatus of claim 11, wherein each of said local regions of said lens has a local curvature.

13. The apparatus of claim 11, wherein said actuating elements comprise a plurality of electrodes disposed at different portions of said lens.

14. The apparatus of claim 13, wherein said electrodes are disposed in a two dimensional array.

15. The apparatus of claim 14, wherein said two-dimensional array is a rectilinear array.

16. The apparatus of claim 1, wherein said rangefinder comprises a transducer for detecting a stimulus from an anatomic structure in an eye, said stimulus being indicative of a range to said object-of-regard.

17. The apparatus of claim 16, wherein said transducer is a pressure transducer for detecting contraction of a muscle.

18. The apparatus of claim 17, wherein said pressure transducer is a piezoelectric element that generates a voltage in response to contraction of said muscle.

19. The apparatus of claim 17, wherein said transducer is an electromyograph for detecting electrical activity associated with contraction of said muscle.

20. The apparatus of claim 16, wherein said transducer is configured to detect a stimulus from an anatomic structure selected from a group consisting of:
   contraction of a ciliary muscle,
   tension in a zonule,
   mechanical disturbance of a lens bag,
   contraction of a rectus muscle,
   dilation of an iris, and
   contraction of an iris.

21. The apparatus of claim 1, wherein said rangefinder comprises an auto focus system.

22. The apparatus of claim 21, wherein said autofocus system comprises:
   an infrared transmitter for illuminating an object with an infrared beam;
   an infrared receiver for receiving a reflected beam from said object, and
   a processor coupled to said infrared receiver for estimating a range to said object on the basis of said reflected beam.

23. The apparatus of claim 21, wherein said rangefinder further comprises a feedback loop coupled to said autofocus system.

24. The apparatus of claim 23, wherein said feedback loop comprises:
   a first lenslet disposed posterior to said lens, said first lenslet having a first focal length;
   a second lenslet disposed posterior to said lens, said second lenslet having a second focal length;
   a first photodetector disposed posterior to said first lenslet, said first photodetector in optical communication with said first lenslet and separated therefrom by a selected distance, said selected distance being between said first and second focal length; and
   a second photodetector disposed posterior to said second lenslet, said second photodetector in optical communication with said second lenslet and separated therefrom by said selected distance;
   a differencing element coupled to outputs of said first and second photodetectors for determining a difference between signals present on said first and second photodetectors, said difference being indicative of an extent to which said lens is focused on said object-of-regard.

25. The apparatus of claim 1, further comprising a manual focusing control for enabling a patient to fine tune focusing of said lens.

26. The apparatus of claim 1, further comprising a power supply for providing power to said rangefinder and said actuator.

27. The apparatus of claim 26, wherein said power supply comprises a battery.

28. The apparatus of claim 27, wherein said battery is adapted for implantation beneath the conjunctiva.

29. The apparatus of claims 27, wherein said power supply comprises a rechargeable battery.

30. The apparatus of claim 29, further comprising a photvoltaic cell configured to recharge said rechargeable battery.

31. The apparatus of claim 26, wherein said power supply comprises a photovoltaic cell.

32. The apparatus of claim 31, wherein said photovoltaic cell is configured for implantation in a cornea.

33. The apparatus of claim 31, wherein said photovoltaic cell is configured for mounting on said lens.

34. An apparatus comprising:
   a lens having an index of refraction that varies in response to a focusing stimulus;
   an actuator in communication with said lens for providing said focusing stimulus;
   a rangefinder for generating, from a range estimate, a relative distance to an object-of-regard, the rangefinder including a pressure-sensitive electromyograph for detecting electrical activity associated with contraction of a muscle, said electrical activity being indicative of a range to said object-of-regard; and
   a controller coupled to said rangefinder and to said actuator for causing said actuator to generate a focusing stimulus on the basis of said range estimate.

35. The apparatus of claim 34, wherein said lens is adapted for implantation in an eye of a human patient.

36. The apparatus of claim 35, wherein said lens is adapted for implantation at a location in an eye, said location being selected from the group consisting of:
   the anterior chamber;
   the posterior chamber;
   the lens bag; and
   the cornea.

37. The apparatus of claim 35, wherein said lens is adapted for implantation in an aphakic human patient.

38. The apparatus of claim 35, wherein said lens is adapted for implantation in a phakic human patient.

39. The apparatus of claim 34, wherein said lens is a foldable lens having a tendency to spring back into an unfolded state.

40. The apparatus of claim 34, wherein said lens comprises a chamber containing nematic liquid crystal.

41. The apparatus of claim 40, wherein said chamber comprises a first planar side and a second planar side opposed to said first planar side, said first and second planar sides being separated by a gap smaller than a separation between a lens bag in an eye and an iris in said eye.

42. The apparatus of claim 34, wherein said lens comprises:
   a first lens element;
   a second lens element moveable relative to said first lens element; and
   a motor coupled to said second lens element for moving said second lens element relative to said first lens element.

43. The apparatus of claim 34, wherein said actuator comprises a variable voltage source.

44. The apparatus of claim 43, wherein said actuator further comprises an electrode coupled to said variable voltage source and to said lens for applying an electric field within said lens.

45. The apparatus of claim 34, wherein said actuator comprises a plurality of actuating elements coupled to different local regions of said lens for selectively varying said index of refraction at said different local regions of said lens.

46. The apparatus of claim 45, wherein each of said local regions of said lens has a local curvature.

47. The apparatus of claim 45, wherein said actuating elements comprise a plurality of electrodes disposed at different portions of said lens.

48. The apparatus of claim 47, wherein said electrodes are disposed in a two dimensional array.

49. The apparatus of claim 48, wherein said two-dimensional array is a rectilinear array.

50. The apparatus of claim 34, wherein said pressure-sensitive electromyograph comprises a piezoelectric element that generates a voltage in response to contraction of said muscle.

51. The apparatus of claim 34, wherein said electromyograph is configured to detect a stimulus from an anatomic structure selected from a group consisting of:
    contraction of a ciliary muscle,
    tension in a zonule,
    mechanical disturbance of a lens bag,
    contraction of a rectus muscle,
    dilation of an iris, and
    contraction of an iris.

52. The apparatus of claim 34, further comprising a manual focusing control for enabling a patient to fine tune focusing of said lens.

53. The apparatus of claim 34, further comprising a power supply for providing power to said rangefinder and said actuator.

54. The apparatus of claim 53, wherein said power supply comprises a battery.

55. The apparatus of claim 54, wherein said battery is adapted for implantation beneath the conjunctiva.

56. The apparatus of claim 54, wherein said power supply comprises a rechargeable battery.

57. The apparatus of claim 56, further comprising a photvoltaic cell configured to recharge said rechargeable battery.

58. The apparatus of claim 53, wherein said power supply comprises a photovoltaic cell.

59. The apparatus of claim 58, wherein said photovoltaic cell is configured for implantation in a cornea.

60. The apparatus of claim 58, wherein said photovoltaic cell is configured for mounting on said lens.

61. The apparatus of claim 34, wherein said lens comprises a plurality of local regions, each of said local regions having a local curvature.

62. The apparatus of claim 61, wherein said actuator includes a plurality of actuating elements, each of said actuating elements in communication with a subset of said local regions.

63. The apparatus of claim 62, wherein said actuating elements are independently addressable.

64. The apparatus of claim 62, wherein said actuating elements are disposed in a two-dimensional array on said lens.

65. The apparatus of claim 34, further comprising a manual focusing control coupled to said actuator for enabling a wearer of said lens to control said focusing stimulus.

66. An apparatus comprising:
    a lens having an index of refraction that varies in response to a focusing stimulus;
    an actuator in communication with said lens for providing said focusing stimulus;
    a rangefinder for generating, from a range estimate, a relative distance to an object-of-regard, the rangefinder including an autofocus system and a feedback loop coupled to said autofocus system, the feedback loop having
        a first lenslet disposed posterior to said lens, said first lenslet having a first focal length;
        a second lenslet disposed posterior to said lens, said second lenslet having a second focal length;
        a first photodetector disposed posterior to said first lenslet, said first photodetector in optical communication with said first lenslet and separated therefrom by a selected distance, said selected distance being between said first and second focal length; and
        a second photodetector disposed posterior to said second lenslet, said second photodetector in optical communication with said second lenslet and separated therefrom by said selected distance;
        a differencing element coupled to outputs of said first and second photodetectors for determining a difference between signals present on said first and second photodetectors, said difference being indicative of an extent to which said lens is focused on said object-of-regard; and
    a controller coupled to said rangefinder and to said actuator for causing said actuator to generate a focusing stimulus on the basis of said range estimate.

67. The apparatus of claim 66, wherein said lens is adapted for implantation in an eye of a human patient.

68. The apparatus of claim 67, wherein said lens is adapted for implantation at a location in an eye, said location being selected from the group consisting of:
    the anterior chamber;
    the posterior chamber;
    the lens bag; and
    the cornea.

69. The apparatus of claim 67, wherein said lens is adapted for implantation in an aphakic human patient.

70. The apparatus of claim 67, wherein said lens is adapted for implantation in a phakic human patient.

71. The apparatus of claim 66, wherein said lens is a foldable lens having a tendency to spring back into an unfolded state.

72. The apparatus of claim 66, wherein said lens comprises a chamber containing nematic liquid crystal.

73. The apparatus of claim 72, wherein said chamber comprises a first planar side and a second planar side opposed to said first planar side, said first and second planar sides being separated by a gap smaller than a separation between a lens bag in an eye and an iris in said eye.

74. The apparatus of claim 66, wherein said lens comprises:
    a first lens element;
    a second lens element moveable relative to said first lens element; and
    a motor coupled to said second lens element for moving said second lens element relative to said first lens element.

75. The apparatus of claim 66, wherein said actuator comprises a variable voltage source.

76. The apparatus of claim 75, wherein said actuator further comprises an electrode coupled to said variable voltage source and to said lens for applying an electric field within said lens.

77. The apparatus of claim 66, wherein said actuator comprises a plurality of actuating elements coupled to different local regions of said lens for selectively varying said index of refraction at said different local regions of said lens.

78. The apparatus of claim 77, wherein each of said local regions of said lens has a local curvature.

79. The apparatus of claim 77, wherein said actuating elements comprise a plurality of electrodes disposed at different portions of said lens.

80. The apparatus of claim 79, wherein said electrodes are disposed in a two dimensional array.

81. The apparatus of claim 80, wherein said two-dimensional array is a rectilinear array.

82. The apparatus of claim 66, wherein said autofocus system comprises:

an infrared transmitter for illuminating an object with an infrared beam;

an infrared receiver for receiving a reflected beam from said object, and a processor coupled to said infrared receiver for estimating a range to said object on the basis of said reflected beam.

83. The apparatus of claim 66, further comprising a manual focusing control for enabling a patient to fine tune focusing of said lens.

84. The apparatus of claim 66, further comprising a power supply for providing power to said rangefinder and said actuator.

85. The apparatus of claim 84, wherein said power supply comprises a battery.

86. The apparatus of claim 85, wherein said battery is adapted for implantation beneath the conjunctiva.

87. The apparatus of claim 85, wherein said power supply comprises a rechargeable battery.

88. The apparatus of claim 87, further comprising a photovoltaic cell configured to recharge said rechargeable battery.

89. The apparatus of claim 84, wherein said power supply comprises a photovoltaic cell.

90. The apparatus of claim 89, wherein said photovoltaic cell is configured for implantation in a cornea.

91. The apparatus of claim 89, wherein said photovoltaic cell is configured for mounting on said lens.

92. The apparatus of claim 66, wherein said lens comprises a plurality of local regions, each of said local regions having a local curvature.

93. The apparatus of claim 92, wherein said actuator includes a plurality of actuating elements, each of said actuating elements in communication with a subset of aid local regions.

94. The apparatus of claim 93, wherein said actuating elements are independently addressable.

95. The apparatus of claim 93, wherein said actuating elements are disposed in a two-dimensional array on said lens.

96. The apparatus of claim 66, further comprising a manual focusing control coupled to said actuator for enabling a wearer of said lens to control said focusing stimulus.

* * * * *